United States Patent [19]

Silvis et al.

[11] Patent Number: 4,837,293
[45] Date of Patent: Jun. 6, 1989

[54] LINEAR BISPHENOL EPOXY POLYMERS CONTAINING CYANO GROUPS

[75] Inventors: H. Craig Silvis; Steven P. Crain; Bassam S. Nader, all of Midland, Mich.

[73] Assignee: The Dow Chemical Company, Midland, Mich.

[21] Appl. No.: 90,643

[22] Filed: Aug. 28, 1987

[51] Int. Cl.$^4$ .............................................. C08G 59/28
[52] U.S. Cl. ...................................................... 528/99
[58] Field of Search ........................................... 528/99

[56] References Cited

U.S. PATENT DOCUMENTS

| | | | |
|---|---|---|---|
| 2,740,806 | 4/1956 | Rorig | 558/410 |
| 3,810,933 | 5/1974 | Banucci | 558/409 |
| 4,609,686 | 9/1986 | Giordano | 528/99 |
| 4,647,648 | 3/1987 | Silvis et al. | 528/102 |
| 4,672,102 | 6/1987 | Silvis et al. | 528/97 |

FOREIGN PATENT DOCUMENTS

| | | |
|---|---|---|
| 1151512 | 7/1963 | Fed. Rep. of Germany . |
| 42-13022 | 7/1967 | Japan . |
| 43-21557 | 9/1968 | Japan . |
| 53-47551 | 7/1973 | Japan . |
| 33123 | 2/1974 | Japan . |
| 47770 | 9/1983 | Japan . |

OTHER PUBLICATIONS

Clemo et al., "Constitution of Santonin. I Synthesis of disantonous acid", 1929, *J. Chem. Soc.* 2368, 2376 (1929).

Reinking et al., "Polyhydroxy Ethers, I Effect of Structure on Properties of High Molecular Weight Polymers from Dihydric Phenols and Epichlorohydrin," 7 *J. Applied Poly. Sci.* 2135 (1963).

Reinking et al., "Polyhydroxy Ethers, II, Effect of Structure on Properties of High Molecular Weight Copolymers from Dihydric Phenol Mixtures and Epichlorohydrin," 7 *J. Applied Poly. Sci.* 2145 (1963).

Banucci, "Cyanopolyesters," 11 *J. Poly. Sci. Poly Chem. Ed.* 2947 (1973).

Banucci, "Dicyanobisphenol Polycarbonate," 6 *Macromol. Synth.* 63 (1977).

*Primary Examiner*—John Kight
*Assistant Examiner*—Frederick Krass

[57] ABSTRACT

Cyanobisphenols of the formula:

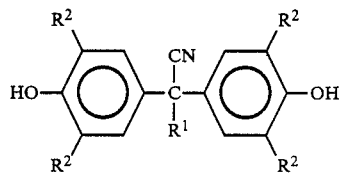

and their diglycidyl ethers may form linear thermoplastic polymers with low oxygen permeability and which contain cyano moieties that may subsequently be reacted to form useful active sites on the polymer.

26 Claims, No Drawings

LINEAR BISPHENOL EPOXY POLYMERS CONTAINING CYANO GROUPS

BACKGROUND OF THE INVENTION

The present invention relates to epoxy monomers and thermoplastic polymer products thereof.

Thermoplastic polymers made by reacting diglycidyl monomers with aromatic diols are well known. See, e.g., N. H. Reinking, et al., "Polyhydroxyethers. I. Effect of Structure on Properties of High Molecular Weight Polymers from Dihydric Phenols and Epichlorohydrin", 7 J. Applied Polymer Sci. 2135 (1963) and N. H. Reinking, et al., "Polyhydroxyethers. II. Effect of Structure on Properties of High Molecular Weight Copolymers from Dihydric Phenol Mixtures and Epichlorohydrin", 7 J. Applied Polymer Sci. 2145 (1963). For example, bisphenol A, diglycidyl ether of bisphenol A and a polymer formed by the reaction of those two compounds are all commercially available.

It would be advantageous to improve upon certain properties of known thermoplastic epoxy polymers. First, polymers with better oxygen barrier properties would be desirable. Second, current technology does not provide a mechanism to place particular active sites, such as an amine or a carboxylic acid moiety, on a thermoplastic epoxy polymer.

SUMMARY OF THE INVENTION

In one aspect, the present invention is a thermoplastic polymeric composition comprising a plurality of cyanobisphenoxy moieties. By cyanobisphenoxy moiety is meant a moiety wherein two phenoxy groups and a cyano group are bonded to an alkyl moiety. Except as otherwise specified, both the phenoxy groups and the alkyl moiety may be substituted with substituents that are inert with respect to alcohols, phenols and oxiranes up to a temperature of about 200° C.

A second aspect of the present invention is a process wherein a cyanobisphenoxy polymer is prepared either by the reaction of a cyanobisphenol with a diglycidyl ether or by the reaction of a cyanobisphenol diglycidyl ether derivative with a diol which contains two phenolic hydroxide moieties.

A third aspect of this invention is a bis(4-hydroxy-3,5-alkylphenyl)acetonitrile and a process for preparing such cyanobisphenols wherein (1) 3,5-dialkyl-4-hydroxybenzaldehyde reacts with a cyanide salt in the absence of sodium bisulfite; and
(2) the product of that reaction reacts with 2,6-dialkylphenol in the presence of acid to form the desired product.

The compositions of the present invention are thermoplastic polymers with a low oxygen permeability and may be used as oxygen barrier films and gas separation membranes. The cyano groups present in the polymer can also be converted to other useful active sites. Therefore, the polymers are intermediates to useful active resins. The first process of the present invention is a process useful for making the previously mentioned compositions. The compound aspect of the invention is a cyanobisphenol which may be used in connection with the present invention, and the second process of the present invention is a process useful to make such compounds.

DETAILED DESCRIPTION OF THE INVENTION

Compositions of the Present Invention

Cyanobisphenoxy moieties found in thermoplastic polymers of the present invention preferably conform to the following formula:

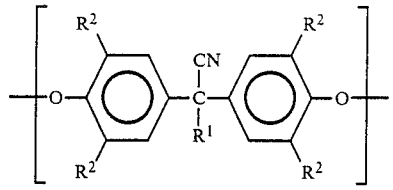

wherein $R^1$ is either hydrogen or alkyl, and each $R^2$ is independently hydrogen, alkyl, alkoxy or halogen. Alkyl and alkoxy groups in $R^1$ and $R^2$ preferably contain up to about six carbon atoms.

Compositions of the present invention will ordinarily contain cyanobisphenoxy moieties wherein at least one phenolic oxygen is bonded to a hydroxyalkyl moiety which serves as a bridge to adjacent units. The cyanobisphenoxy and hydroxyalkyl moieties preferably conform to the formula:

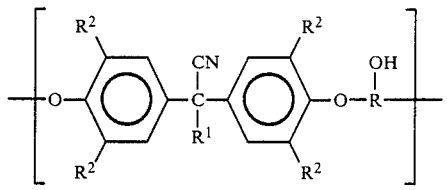

wherein $R^1$ and $R^2$ each conform to the previous definition and R is a trivalent lower alkyl group of at least 3 carbon atoms. R more preferably contains no more than about 5 carbon atoms and most preferably is a trivalent propyl group with the hydroxyl group attached to the second carbon atom. $R^1$ is more preferably hydrogen or an alkyl group containing no more than about four carbons, and most preferably hydrogen or methyl. Each $R^2$ is more preferably independently hydrogen, chlorine, bromine, methoxy, ethoxy or an alkyl group of no more than three carbons, and is most preferably independently hydrogen or a methyl group.

Compositions of the instant invention may preferably contain only cyanobisphenoxy units, in which case they more preferably conform to the formula:

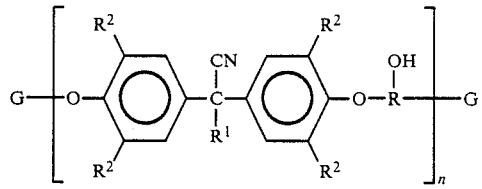

wherein n is a number of recurring units greater than one, each G is an end group, and the limitations and preferred embodiments of other substituents are as previously defined. The average value of n is preferably at least about 30, more preferably at least about 100, and most preferably at least about 350. Each G is preferably independently hydrogen, an oxirane moiety, or the remnant of an oxirane moiety. Each G is most preferably hydrogen. R, $R^1$ and $R^2$ groups in different recurring units on a polymer chain may be the same or different.

Compositions of the instant invention also preferably contain cyanobisphenoxy moieties with other organic units which are inert with respect to alcohols, phenolics and epoxides up to temperatures of 200° C. Such compositions will more preferably conform to the formula:

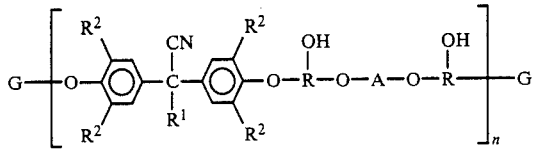

wherein A is a divalent organic moiety which is inert with respect to alcohols, phenolics and epoxides up to temperatures of 200° C., n is a number of recurring units greater than one and the other substituents have the limitations and preferred embodiments set out above. The average "n" is preferably at least about 30, more preferably at least about 100, and most preferably at least about 350. A, R, $R^1$ and $R^2$ groups in different recurring units on a polymer chain may be the same or different.

The unit "A" preferably comprises an aromatic moiety or moieties. More preferably A conforms to the formula:

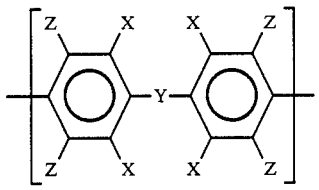

wherein Y is a divalent lower alkyl, carbonyl, sulfonyl, oxygen or a covalent bond; and each X and Z is independently hydrogen, a halogen or a sterically feasible alkyl moiety. Y is more preferably either a divalent lower alkyl moiety or a covalent bond and most preferably a divalent lower alkyl moiety. Each X is most preferably hydrogen. Each Z is more preferably hydrogen or a methyl or ethyl group and most preferably hydrogen.

In their most preferred embodiments, the compositions of this invention are thermoplastic polymers with glass transition temperatures above about 100° C. They have low permeability to oxygen and contain cyano moieties which can be converted to other functional moieties such as amine groups or carboxylic acid groups.

COMPOUNDS USEFUL IN THE PROCESS OF THE PRESENT INVENTION

Compositions of the present invention may be formed either by the reaction of a cyanobisphenol with a diglycidyl ether or by the reaction of a diol containing two phenolic hydroxyl groups with the diglycidyl ether derivative of a cyanobisphenol. Cyanobisphenols preferably comply with the formula:

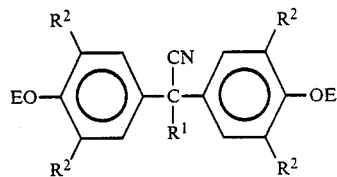

wherein E is either hydrogen or a moiety of the formula:

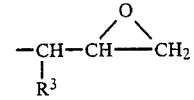

wherein $R^1$ is hydrogen or alkyl; $R^2$ is either hydrogen, alkyl, alkoxy or halogen; and $R^3$ is hydrogen or an alkyl moiety. Preferred embodiments for $R^1$ and $R^2$ are those given for the composition. $R^3$ is preferably hydrogen or an ethyl or methyl group and more preferably hydrogen. Cyanobisphenol monomers and derivative monomers and processes for making them are specifically described hereafter.

CYANOBISPHENOLS AND PREPARATION

Cyanobisphenols used in connection with the present invention preferably conform to the following structural formula:

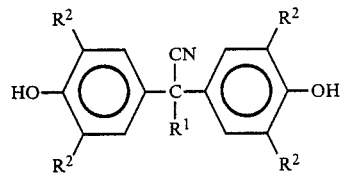

wherein the limitations and preferred embodiments of $R^1$ and $R^2$ are those previously described.

Some cyanobisphenols useful in connection with the present invention are known compounds whose synthesis has been reported in the literature. The precise process for making cyanobisphenols varies depending upon the groups desired in the $R^1$ and $R^2$ positions.

Methods for the preparation of cyanobisphenols wherein $R^1$ is an alkyl group are describe in two sources: Banucci, "Cyanopolyesters", 11 J. Polymer Science 2947 (1973) and Banucci, Bis(3-chloro-4-hydroxyphenyl)mandelonitrile, U.S. Pat. No. 3,810,933 (May 14, 1974). The Banucci references describe a process wherein an appropriate alkyl carbonyl cyanide of the formula:

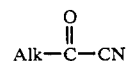

wherein Alk denotes an alkyl group, reacts at 40° C. with two equivalents of an appropriate phenol or orthosubstituted phenol of the formula:

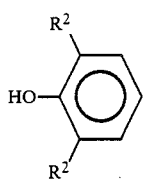

in an anhydrous solution of 100 ml hexane, 60 g polyphosphoric acid and a catalytic amount of β-mercaptothiopropionic acid to form the corresponding cyanobisphenols. Cyanobisphenols prepared according to the preceding process comply with the formula listed below.

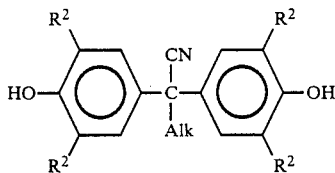

Although Banucci limits his teaching to unsubstituted and alkyl-substituted cyanobisphenols, the same procedures should be effective for preparing halogen-substituted and alkoxy-substituted phenols.

The afore-mentioned process can not advantageously be employed to prepare cyanobisphenols wherein $R^1$ is hydrogen. When $R^1$ and all $R^2$ are hydrogen, the following procedure is effective to prepare the cyanobisphenol. 4-Hydroxybenzaldehyde is reacted with sodium cyanide in the presence of sodium bisulfite to yield 4-hydroxymandelonitrile, a cyanohydrin which has the following formula.

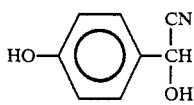

The reaction and conditions are described in Landenberg et al., "Synthesis of 3-Hydroxy-2(3)-Benzofuranone and of 4-Hydroxymandelic Acid", 58 J. Amer Chem Soc. 1292 (1936) and in Taylor, et al, "a-N,N-Dimethylaminophenylacetonitrile", 5 Organic Synthesis 437 (1962). 4-Hydroxymandelonitrile is then reacted with excess phenol in the presence of sulfuric acid at a temperature of about 55° C. to 60° C. to yield bis-(4-hydroxyphenyl)acetonitrile:

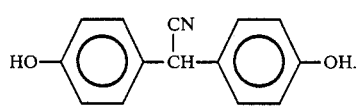

A description of the reaction and its conditions is found in Schraufstätter, "Darstellung und Reaktionen von 4,4'-Dihydroxydiphenylacetonitril", 295 Arch. Pharm. 269 (1962).

The same procedure is not readily used to prepare a cyanobisphenol wherein each $R^2$ position contains an alkyl moiety. Under the conditions described by Landenberg, et al, cyanide apparently does not add to the alkyl-substituted hydroxybenzaldehyde. However, it has unexpectedly been discovered that a similar process carried out in an ethanol and water solution in the absence of sodium bisulfite will add a cyano group to the benzaldehyde.

Alkyl-substituted hydroxybenzaldehyde is prepared from a 1,3-dialkylphenol by a process reported in Nikiforov, et al., 1962 Izv. Akad. Nauk. Otd. Khim. Nauk 1836 (1962). Procedures described in Allen et al., 4 Organic Synthesis 866 (1966), can be used to prepare alkyl or alkoxy-substituted hydroxybenzaldehyde. The substituted hydroxybenzaldehyde is suspended in a mixture of ethanol and water, preferably in about equal portions of water and ethanol by volume. Alkali metal cyanide is added, preferably in one addition. The alkali metal cyanide is preferably potassium cyanide. The amount of cyanide used is preferably a slight molar excess over the hydroxybenzaldehyde. The reaction may be run at any temperature at which it proceeds, but is most conveniently run at room temperature.

After allowing sufficient time for all of the benzaldehyde to react, the mandelonitrile product is reacted in situ in the presence of acid with an appropriate substituted phenol. The acid is preferably concentrated sulfuric acid. The phenol is more preferably added in a solution with concentrated sulfuric acid with stirring. A molar excess of phenol is preferably used. After allowing sufficient time for the reaction to be completed, the products may be recovered and purified by known methods.

The procedures and preferred embodiments described above may also be used to prepare halogen-substituted cyano bisphenols. Futhermore, obvious variations in the phenols and other reagents used will permit the skilled artisan to prepare asymmetric cyanobisphenols wherein one phenol moiety contains alkyl substituents and the other does not or wherein each contains different alkyl substituents. Cyanobisphenols prepared by the procedures set out above may be used as monomers to make compositions of the present invention.

DIGLYCIDYL ETHERS OF CYANOBISPHENOLS

Diglycidyl ethers of the cyanobisphenols described hereinbefore are also useful monomers for the present invention. Diglycidly ethers preferably conform to the following formula:

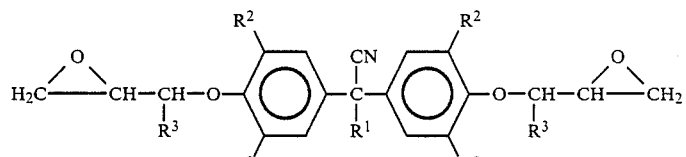

wherein $R^1$, $R^2$ and $R^3$ each independently have the same embodiments and preferred embodiments as described hereinbefore.

The preparation of a glycidyl ether from a phenolic compound and an epihalohydrin is a reaction well-known in the art. The epihalohydrin is preferably epichlorohydrin. A cyanobisphenol described hereinbefore is dissolved in a substantial excess, preferably a 20:1 molar excess, of the epihalohydrin. A 20 percent aqueous sodium hydroxide solution is added slowly with stirring at about 40° C. Preferably, a catalytic amount of quaternary alkyl ammonium bromide or chloride salt is also added as a catalyst. After the reaction is completed, the excess epihalohydrin is removed by known techniques, such as rotoevaporation. The product is dissolved in methylene chloride and washed with water to remove water-soluble impurities. The cyanobisphenol diglycidyl ether is then recovered from the methylene chloride by known methods, such as rotoevaporation.

PROCESS FOR MAKING COMPOSITIONS

Compositions of the present invention are formed by contacting a diglycidyl ether and a diol containing two phenolic hydroxide moieties, at least one of which is a cyanobishphenol or diglycidyl ether thereof, in an organic solvent that is inert with respect to all reagents preferably with a catalyst and preferably at a temperature of between about 125° C. and about 200° C. such that epoxy moieties react with hydroxyl moieties to form a links between the monomers.

The diol monomer may be a cyanobisphenol of the class described previously, and the epoxy monomer may be a diglycidyl ether of a cyanobisphenol. Such monomers preferably conform to the formulae:

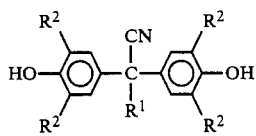

or

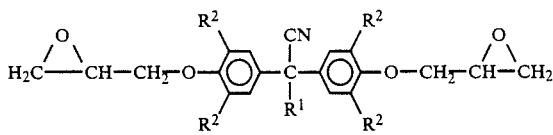

and form polymers of the formula:

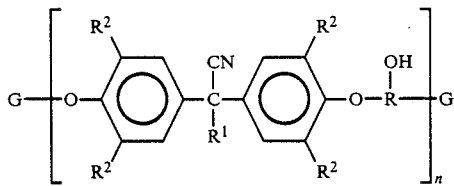

wherein $R^1$, $R^2$, R and G have the meanings and preferred limitations described previously.

Copolymers may also be formed by reaction of a cyano-containing monomer described previously with a comonomer which does not contain a cyano moiety. Cyano-containing monomers preferably conform to the formula:

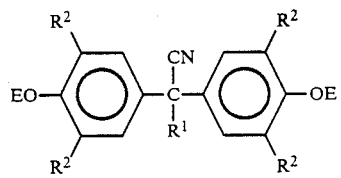

wherein all substituents have the meanings previously given. Comonomers preferably conform to the formula:

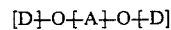

wherein:
when E is a hydrogen, D is an epoxide and A is a divalent organic moiety with the meaning and preferred limitations previously used to describe A in describing compositions of the present invention; and
when E is an epoxide, D is hydrogen and A is a divalent organic moiety with an aromatic moiety or moieties bonded to the two oxygens which otherwise has the limitations and preferred embodiments previously used to describe A.

Copolymers thus formed preferably comply with the formula:

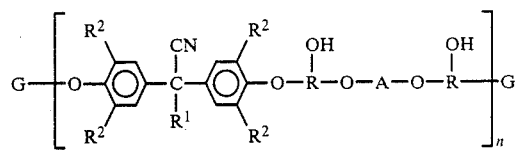

The most preferred comonomers comply with one of the two following sets of formulae:

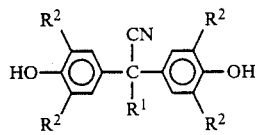

and

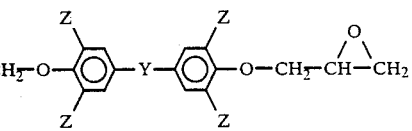

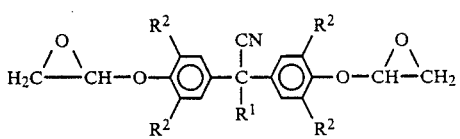

and

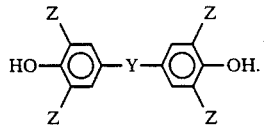

wherein the meanings and preferred limitations of each substituent are as previously described. For example, cyanobisphenols may be polymerized with diglycidyl ethers of bisphenol A, which are commercially available. Cyanobisphenol diglycidyl ethers may be polymerized with known aromatic diols such as bisphenol A and hydroquinone.

The reaction of the chosen monomers preferably takes place in an organic solvent which is inert with respect to all reagents. The solvent is more preferably a propylene gylcol ether. Examples of appropriate solvents are dipropylene glycol monomethyl ether, sold as DOWANOL DPM ® and propylene glycol monomethyl ether, sold as DOWANOL PPH ®. The solvent must be free of water. An anhydrous solvent may preferably be obtained by taking the center cut from solvent distilled from potassium carbonate or a mixture of potassium carbonate and stannous chloride.

Polymerization preferably takes place under an inert atmosphere. The atmosphere is more preferably nitrogen. Noble gases may also be used to create an inert atmosphere.

Preferably, approximately equimolar amounts of monomer are used. More preferably, a slight excess of the diglycidyl monomer is used.

A catalytic amount of catalyst is also preferably used. The catalyst may be any substance known in the art to catalyze the reaction of oxiranes and phenolic hydroxyl groups. Ethyltriphenyl phosphonium acetate is the most preferred catalyst. Other potential catalysts include quaternary alkyl phosphonium and quaternary alkyl ammonium chloride and bromide salts.

Polymerization may be run at any temperature at which the glycidyl ether moieties will react with the phenolic moieties. The temperature is preferably at least about 125° C. and more preferably at least about 140° C. The temperature is preferably at most about 200° C., more preferably at most about 180° C. and most preferably at most about 160° C.

A preferred method to carry out polymerization is to combine the solvent, diol and ether in a reaction vessel under an inert atmosphere, raise the temperature in the reaction vessel to the desired temperature, and to slowly add the catalyst. Preferably, the reaction mixture is stirred as the catalyst is added. It may become necessary to add further solvent to the reaction mixture as catalyst is added in order to keep polymer which forms from tying up the stirrer.

The polymer formed in the reaction may be recovered and purified by known methods. Preferably, the reaction mixture is diluted with tetrahydrofuran and the dissolved polymer is precipitated by adding methanol or a solution containing equal amounts by volume of methanol and water. The reaction yields the linear polymers described previously.

ILLUSTRATIVE EXAMPLES

The following examples are for illustrative purposes only and are not to be taken as limiting the scope of either the specification or the claims.

EXAMPLE 1

Preparation of
Bis-(4-hydroxy-3,5-dimethylphenyl)acetonitrile

Five grams of 3,5-dimethyl-4-hydroxybenzaldehyde is suspended with stirring in 20 ml of 50% by volume aqueous ethanol. 2.6 gm of potassium cyanide is added in one addition. After one hour, a freshly prepared solution of 6 gm 2,6-dimethylphenol in 10 ml of concentrated sulfuric acid is added slowly over a period of about one minute. An exothermic reaction takes place. After stirring for one hour, the mixture is poured into 100 ml of water. A brown solid containing the named product is filtered off and washed with water. It is dissolved in 10 ml tetrahydrofuran and stirred vigorously for several hours with a solution of 10 gm sodium bisulfite in 50 ml of water. The product is subsequently extracted with ether, washed with brine, dried with magnesium sulfate, filtered and concentrated to yield 5.81 grams of the title compound, a yellow solid.

EXAMPLE 2

Polymer of
Bis-(4-hydroxy-3,5-dimethylphenyl)acetonitrile and
diglycidyl ether thereof A 50 ml resin kettle is charged with 5 ml of DOWANOL PPH ® solvent which has distilled from a mixture with anhydrous potassium carbonate and stannous chloride to eliminate water. Bis-(4-hydroxy-3,5-dimethyl-)acetonitrile (1.4928 g) and 2.1895 g of a diglycidyl ether derived from the same compound are placed in the kettle under nitrogen atmosphere. The kettle is heated to 120° C. and 4 drops of A-1 TM catalyst (an ethyltriphenyl phosphonium acetate solution) from Alpha Ventron Co. are added. Through the course of the reaction, the solution turns a dark blue-green color. After 16½ hours, the solution is cooled and a mixture of 20 ml of tetrahydrofuran and 5 ml of acetic acid is added. The solution turns yellow. The title polymer is precipitated by pouring the solution into a mixture of equal volumes of methanol and water, and the polymer is chopped up in a blender. The polymer is then recovered by filtration and dried at reduced pressure and 150° C. Bis-(4-hydroxy-3,5-dimethyl)acetonitrile (3.5 g) is collected, which has a glass transition temperature of 144.5° C.

EXAMPLE 3

Polymer of bis-(4-hydroxyphenyl)acetontrile and
diglycidyl ether thereof

Bis-(4-hydroxyphenyl)acentonitrile (2.559 g), 4.025 g of the corresponding diglycidyl ether and 10 ml of DOWANOL PPH ® solvent are added to a 50-ml resin kettle under nitrogen atmosphere. The slurry is heated to approximately 120° C. and 5 drops of A-1# catalyst from Alpha Ventron Co. are added. The reaction mixture is heated to 180° C. and extra solvent is added as necessary. After 4 hours, the reaction solution is cooled and diluted with tetrahydrofuran. The polymer is precipitated by adding this solution to a mixture of 3 parts methanol by volume and 1 part water by volume and recovered by filtration. After vacuum drying, 6.2 g of the title polymer is recovered. The polymer has a glass transition temperature of 121° C. $M_w = 79,400$.

EXAMPLE 4

Polymer of bis-(4-hydroxyphenyl)-acetonitrile and
Bisphenol A diglycidyl ether

A 50-ml resin kettle equipped with an overhead stirrer and a nitrogen inlet tube is purged with nitrogen and charged with 4.068 g of bis-(4-hydroxyphenyl)acetonitrile, 6.300 g of bisphenol A diglycidyl ether and 8 ml of DOWANOL DPM° solvent. The stirred mixture is heated to approximately 140° C. and 80 ml of A-1 TM catalyst is added. Subsequent viscosity buildup is compensated for by continual addition of further DOWANOL DPM ® solvent. After 4 hours, the solution is cooled to room temperature and diluted with 50 ml of tetrahydrofuran. The title polymer is precipitated into 200 ml of an equal volume mixture of methanol and water. The polymer is recovered by filtration and dried under vacuum at 100° C. for 12 hours to yield 9.4 g of the title polymer.

What is claimed is:

1. A thermoplastic polymer comprising a plurality of cyanobisphenoxy units which conform to the formula:

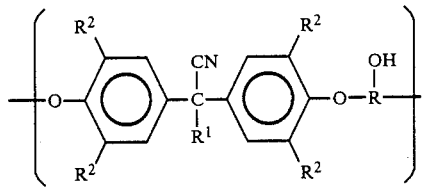

wherein $R^1$ is either hydrogen or alkyl, each $R^2$ is independently hydrogen, alkyl, alkoxy or halogen, and R is an alkyl group of at least 3 carbons.

2. The polymer of claim 1 wherein R is no more than about 5 carbons, $R^1$ is hydrogen or alkyl of no more than about 4 carbons and each $R^2$ is independently hydrogen, chlorine, bromine, methoxy, ethoxy or alkyl of no more than about 3 carbons.

3. The polymer of claim 2 wherein R is a propyl group, $R^1$ is hydrogen or methyl and each $R^2$ is independently hydrogen or methyl.

4. The polymer of claim 3 wherein the moiety shown results either from the reaction of an epoxy moiety with a bisphenol which complies with the formula:

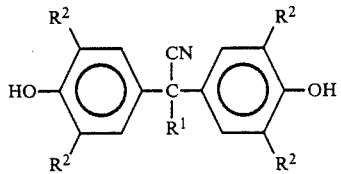

or from the reaction of a glycidyl ether of such a compound with a diol which contains two phenolic hydroxide moieties.

5. The polymer of claim 1 which complies with the formula:

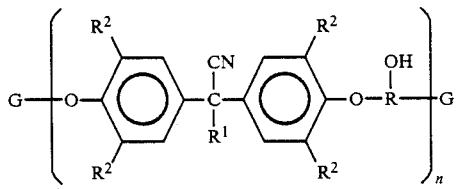

wherein n is a number of recurring units greater than one, and G is hydrogen, an oxirane group or the remnant of an oxirane group.

6. The polymer of claim 5 wherein R is no more than about 5 carbons, $R^1$ is hydrogen or alkyl of no more than about 4 carbons and each $R^2$ is independently hydrogen, chlorine, bromine, methoxy, ethoxy or alkyl of no more than about 3 carbons.

7. The polymer of claim 6 wherein n is 30 or more.

8. The polymer of claim 7 wherein R is a propyl group, $R^1$ is hydrogen or methyl and each $R^2$ is independently hydrogen or methyl.

9. The polymer of claim 8 which has been formed by a reaction of two monomers which comply with the following formulae:

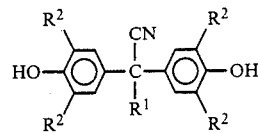

and

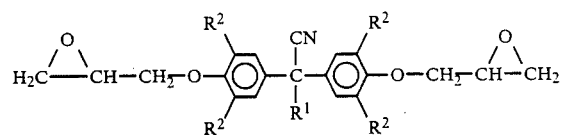

10. The polymer of claim 1 which complies with the formula:

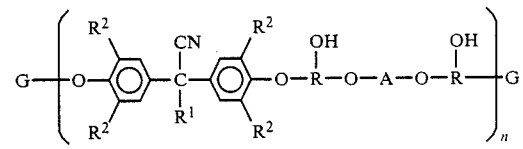

wherein A is a divalent organic moiety and n is a number of recurring units greater than one, and G is hydrogen, an oxirane group or the remnant of an oxirane group.

11. The polymer of claim 10 wherein R is no more than about 5 carbons, $R^1$ hydrogen or alkyl of no more than about 4 carbons and each $R^2$ is independently hydrogen, chlorine, bromine, methoxy, ethoxy or alkyl of no more than about 3 carbons.

12. The polymer of claim 11 wherein A complies with the formula:

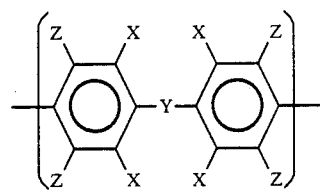

wherein Y is either lower alkyl, carbonyl, sulfonyl, oxygen or a bond; and each X and Z is independently hydrogen, a halogen or an alkyl moiety.

13. The polymer of claim 12 wherein each X is hydrogen, each Z is independently hydrogen, methyl, ethyl, chlorine or bromine, and Y is either alkyl or a bond.

14. The polymer of claim 13 wherein each Z is independently hydrogen or methyl, Y is an alkyl moiety of one to 3 carbons, R is a propyl group, $R^1$ is hydrogen or methyl and each $R^2$ is independently hydrogen or methyl.

15. The polymer of claim 14 which has been formed by a reaction of two monomers which comply with the formulae:

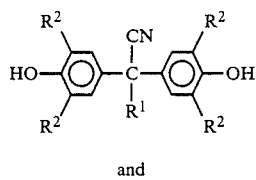

and

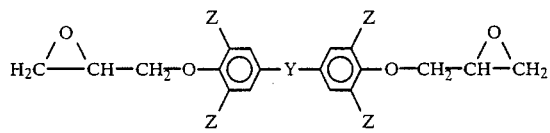

16. The polymer of claim 14 which has been formed by a reaction of two monomers which comply with the formulae:

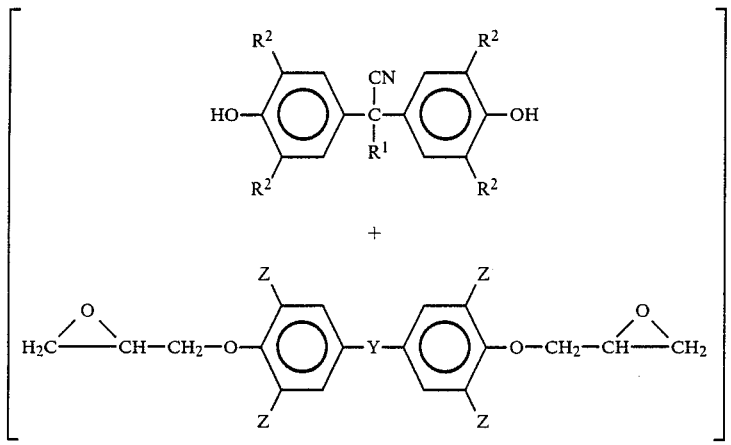

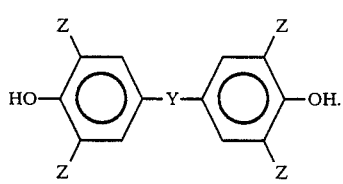

and

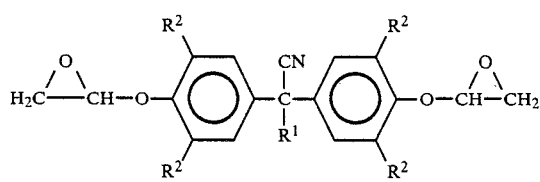

17. A process for forming a thermoplastic cyanobisphenoxy polymer comprising and wherein contacting a diol having two phenolic hydroxide moieties with a diglycidyl ether, at least one of which is a cyanobisphenol or its diglycidyl ether derivative which complies with the formula:

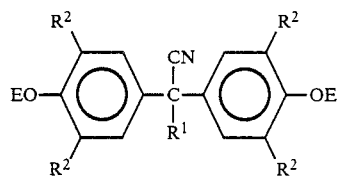

wherein E is either hydrogen or a moiety of the formula:

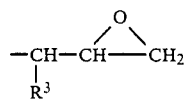

wherein $R^1$ is hydrogen or alkyl, $R^2$ is either hydrogen, alkyl, alkoxy or halogen; and $R^3$ is hydrogen or an alkyl moiety, under conditions such that the epoxy moieties react with the hydroxide moieties to form links between the monomers.

18. The process of claim 17 wherein $R^1$ is hydrogen or alkyl containing one to 4 carbons; each $R^2$ is independently hydrogen, methyl, ethyl, methoxy, ethoxy, chlorine or bromine; and $R^3$ is hydrogen, ethyl or methyl.

19. The process of claim 18 wherein a diol which complies with the given formula when E is H is reacted with a diglycidyl ether which complies with the given formula when E is an epoxide.

20. The process of claim 19 wherein a polymer is formed which complies with the formula:

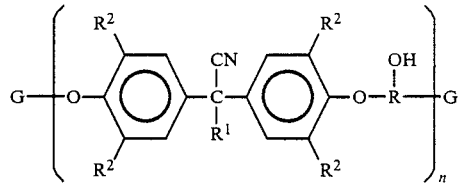

wherein n is a number of recurring units greater than one, and G is hydrogen, an oxirane group or the remnant of an oxirane group.

21. The process of claim 18 wherein the cyanobisphenol or its diglycidyl ether derivative reacts with a comonomer of the formula:

$$(D)-O-(A)-O-(D)$$

wherein
when E is hydrogen, D is an epoxide, and A is a divalent organic moiety which is inert with respect to alcohols, phenolics and epoxides up to temperatures of 200° C.; and
when E is an epoxide, D is hydrogen and A is a divalent organic moiety which is inert with respect to alcohols, phenolics and epoxides up to temperatures of 200° C. having an aromatic moiety or moieties bonded to the two oxygens.

22. The process of claim 21 wherein A complies with the formula:

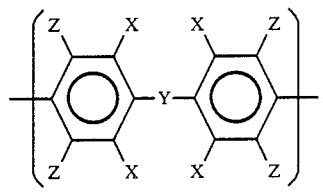

wherein Y is either lower alkyl, carbonyl, sulfonyl, oxygen or a bond; and each X and Z is independently hydrogen, a halogen or an alkyl moiety.

23. The process of claim 22 wherein each X is hydrogen, each Z is independently hydrogen, methyl, ethyl, chlorine or bromine, and Y is either alkyl or a bond.

24. The process of claim 23 wherein a polymer is formed which complies with the formula:

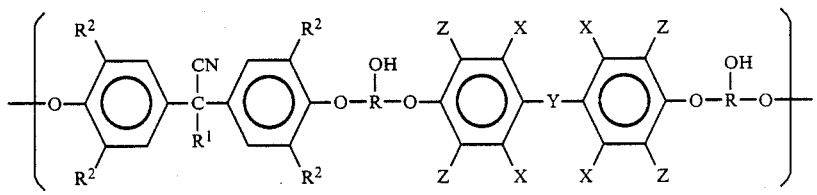

25. The process of claim 24 wherein each Z is independently hydrogen or methyl, Y is an alkyl moiety of one to 3 carbons, R is a propyl group, $R^1$ is hydrogen or methyl and each $R^2$ is independently hydrogen or methyl.

26. The process of claim 25 wherein bis-(4-hydroxyphenyl)acetonitrile or bis-(4-hydroxy-3,5-dimethylphenyl)acetonitrile is reacted with a diglycidyl ether of bisphenol A.

* * * * *

UNITED STATES PATENT AND TRADEMARK OFFICE
CERTIFICATE OF CORRECTION

PATENT NO. : 4,837,293

DATED : June 6, 1989

INVENTOR(S) : H. Craig Silvis, Steven P. Crain, Bassam S. Nader

It is certified that error appears in the above-identified patent and that said Letters Patent is hereby corrected as shown below:

Column 5, line 46, "a-N,N-" should correctly appear as --α-N,N- --.

Column 6, line 16, "1966" should correctly appear as --1962--.

Column 6, line 53, "Diglycidly ethers" should correctly appear as --Diglycidyl ethers--.

Column 7, line 24, "cyanobishphenol" should correctly appear as --cyanobisphenol--.

Column 13, lines 19-37, the formula should not appear.

Column 13, line 64, "and wherein" should not appear.

Signed and Sealed this

Thirty-first Day of July, 1990

Attest:

HARRY F. MANBECK, JR.

Attesting Officer

Commissioner of Patents and Trademarks